(12) United States Patent
Carturan et al.

(10) Patent No.: US 6,214,593 B1
(45) Date of Patent: Apr. 10, 2001

(54) ENCAPSULATION OF SUPPORTED ANIMAL CELLS USING GAS-PHASE INORGANIC ALKOXIDES

(75) Inventors: Giovanni Carturan, Albignasego; Maurizio Muraca, Padua; Renzo Dal Monte, Brendola, all of (IT)

(73) Assignee: Biosil A.G., Vaduz (LI)

( * ) Notice: Subject to any disclaimer, the term of this patent is extended or adjusted under 35 U.S.C. 154(b) by 0 days.

(21) Appl. No.: 09/194,595

(22) PCT Filed: May 28, 1996

(86) PCT No.: PCT/EP96/02265

§ 371 Date: Nov. 27, 1998

§ 102(e) Date: Nov. 27, 1998

(87) PCT Pub. No.: WO97/45537

PCT Pub. Date: Dec. 4, 1997

(51) Int. Cl.[7] .............................. C12N 11/14; C12N 11/04; C12N 5/06; B12N 5/00; A61K 35/12
(52) U.S. Cl. .................. 435/176; 424/93.7; 435/182; 435/382; 435/395; 435/396; 435/397
(58) Field of Search .................................. 435/176, 182, 435/395, 396, 397; 424/93.7

(56) References Cited

FOREIGN PATENT DOCUMENTS

WO 96/36703 * 11/1996 (WO) .

OTHER PUBLICATIONS

G. Carturan et al., "Entrapment of viable microorganisms by $SiO_2$ sol–gel layers on glass surfaces: Trapping, catalytic performance and immobilization durability of *Saccharomyces cerevisae*", Journal of Biotechnology, 30 (1993) 197–210.*

* cited by examiner

*Primary Examiner*—David M. Naff
(74) *Attorney, Agent, or Firm*—Henry D. Coleman; R. Neil Sudol

(57) ABSTRACT

A suspension of animal cells is incubated with supports to adhere the cells to the supports. Preferably, the supports have pores that provide pore volume, and the cells are grown during incubation until most of the available pore volume is filled with cells. An encapsulating layer is then formed around the supported cells by exposing the cells on the supports to a reactive gas composed of a carrier gas such as sterile air saturated with an inorganic alkoxide followed by treatment with steam to hydrolyze residual alkoxide groups. The encapsulated cells are stored by immersion in culture media. The cells may be in the form of cell aggregates, and the supports can be sterilized. The supports and encapsulating layer can have pores of a size that permit free exchange nutrients and metabolic products, and excludes the cells from contacting antibodies or immune cells when implanted. The encapsulated cells can used in an extracorporeal device or implanted directly.

12 Claims, 10 Drawing Sheets

MICROPROBE ANALYSIS OF A SMALL CELL CLUSTER
ON THE MEMBRANE

ENCAPSULATION OF SUPPORTED ANIMAL CELLS USING GAS-PHASE INORGANIC ALKOXIDES

FIELD OF THE INVENTION

The present invention relates to a process for the encapsulation of viable animal cells, suitable for research and industrial applications, including production of artificial organs, tissue and cell transplantation and production of cell derived substances.

BACKGROUND OF THE INVENTION

It is known that loss or failure of organs and tissues can be treated by the development of functional substitutes made by cells placed on or within matrices which can be implanted or used as extracorporeal devices.

Some reviews on this topic are: R. Langer and J. P. Vacanti; Science, 260, 920 (1993); P. E. Lacy, Scientific American, (1995) 40; W. W. Gibbs, Scientific American, (1993) 16.

Some literature reports relevant to the problem are T. R. Shockley and M. L. Yarmush, Biotechnol. Bioeng., 35 (1990) 843; M. Taya, M. Yoshikawa, and T. Kobayashi, J. Ferment. Bioeng., 67 (1989) 138; Y. Shirai, H. Heshimoto, and H. Kawahara, Appl. Microbiol. Biotechnol., 29 (1988) 113; Y. Ho and T. M. S. Chang, Artif. Organs, 16 (1992) 442; A. A. Demetriou et. al., Science, 233 (1986) 1190; F. Lim and A. M. Sun, Science, 210 (1980) 908; E. J. A. Pope, J. Sol-Gel Sci. Tech., 4 (1995) 225; E. J. A. Pope et al. "Sol-Gel Science and Technology", Volume 55 (1955) pages 33–49.

In most cases the encapsulation is performed by hydrogels, in particular polysaccaride alginate, acrylonitrile-vinyl chloride copolymers, hollow fibers, carrageenan gel, agar rods and sol-gel derived $SiO_2$ from hydrolysis of silicon alkoxides in solution.

These approaches are affected by severe shortcomings such as reduction of mass transfer with the medium, insufficient stiffness to avoid cell release, chemical incompatibility with cell viability, production of severe poison byproducts, as for cell encapsulation by sol-gel obtained by hydrolysis and condensation of inorganic alkoxides in solution.

These problems can be solved by reacting supported cells and cell aggregates with gas-phase inorganic alkoxides suitable to react with the cell surface, resulting in a thin porous deposit of inorganic oxides in accordance with PCT application No. PCT/IT95/00083 the content of which is incorporated herewith as reference.

OBJECTS OF THE INVENTION

The aim of the present invention is therefore to avoid the disadvantages of mentioned encapsulation procedures by means of a process which provides a definite encapsulation of viable animal cells by a continuous and permanent layer of inorganic oxides with a pore size distribution ensuring free exchange of nutrients and metabolic products and avoiding antibody and immune-cell invasive action.

Another object of the invention is to provide a general immobilization method for animal cells and cell aggregates without limitations to defined organs, species, and cell functions with preservation of cell viability and metabolic functions.

Still another object of the invention is to provide a method involving simple operations under mild conditions of temperature and pressure which can be performed with industrial-scale devices and production equipments under sterile environmental conditions.

A further object of the invention is the maintenance of viable animal cell and of their specific functions also for use in extra-corporeal devices and the supply of immobilized cell aggregates for transplantation into the body.

DESCRIPTION OF THE INVENTION

These and other objects are achieved, according to the invention by a process for encapsulation of viable animal cells suitable for research and industrial applications, such as production of artificial organs, tissue and cell transplantation and production of cell derived substances, comprising the steps of:

a) providing sterilized supports made of organic and/or inorganic compounds and with suitable geometry to immobilize the desired loads of cells;

b) incubating a cell suspension with the supports in order to ensure adhesion to the support surface;

c) encapsulating the cells with a permanent layer formed by investing the supports with a reactive gas current composed of a carrier gas saturated by inorganic alkoxides for time intervals variable in function of cell nature and load, support geometry and porosity;

d) treating the encapsulated viable cells with steam under mild conditions to perform total hydrolysis of residual alkoxide groups;

e) storing the cells encapsulated on the supports by immersion into appropriate culture media.

Preferably, incubation step b) is accomplished by growing actively replicating cell lines in order to fill most of the available volume of the supports.

Furthermore, the reactive gas of step c) may be composed of a gas carrier saturated by $Si(OR)_4$ and/or $SiX_x(OR)_{4-x}$, where x=1,2; X=H, alkyl or halide; R=alkyl.

It has been surprisingly and conclusively found that it is possible to encapsulate animal cells, in accordance with the present invention.

The supports may be formed from foam of organic polymers, polymeric or glass or ceramic fiber textures, natural products, rock wool, organic or inorganic membranes.

The supports may be shaped as sheets, disks, plates, cones, tubes or corrugated solids with void/middle ratios in the interval 0.1–0.9 due to open pores ranging from 1 $\mu$m to 200 $\mu$m, in diameter.

Supports of inorganic materials, after sterilization, can be dipped into a solution of inorganic-oxide precursors, for example silicon alkoxides, suitable of hydrolysis and condensation. The solution viscosity ranges from 0.1 and 100 Pas, the extraction rate is between 1 and 103 mm/s, the nominal oxide concentration is in the interval 1–100 $g/dm^3$, providing a definite increase of stiffness and mechanical strength, for example of textured glass fibers.

The cell load may be extended up to the available void volume; supports extracted from culture are mounted in a rack and tranferred into a closed reaction chamber. The items are invested by a sterile air flux saturated by reactive alkoxides, preferably a mixture of $HSi(CH_3)(OC_2H_5)_2$ and $Si(OC_2H_5)_4$, at room temperature. Saturation is obtained by bubbling the air flux into the alkoxide mixture kept at temperatures in the interval 10–90° C. The reactive gas flux is variable in function of cell load. The treatment is prolonged for some minutes, then steam is introduced at room temperature for appropriate time intervals.

The treatment with reactive gas, followed by steam reaction can be repeated several times during which the composition of the reactive gaseous species can be modified, for example changing the alkoxides or their concentrations.

These changes can be used to modify the specific surface area and pore size distribution of the deposited layer providing a variable permeability thus affecting the mass transfer as a function of bulkiness and molecular weight.

Further characteristics and advantages of the invention will be come apparent from the description of four examples, illustrated hereinafter only by way of non-limitative examples with reference to the accompanying FIGS. 1 to 11.

Figure 1:
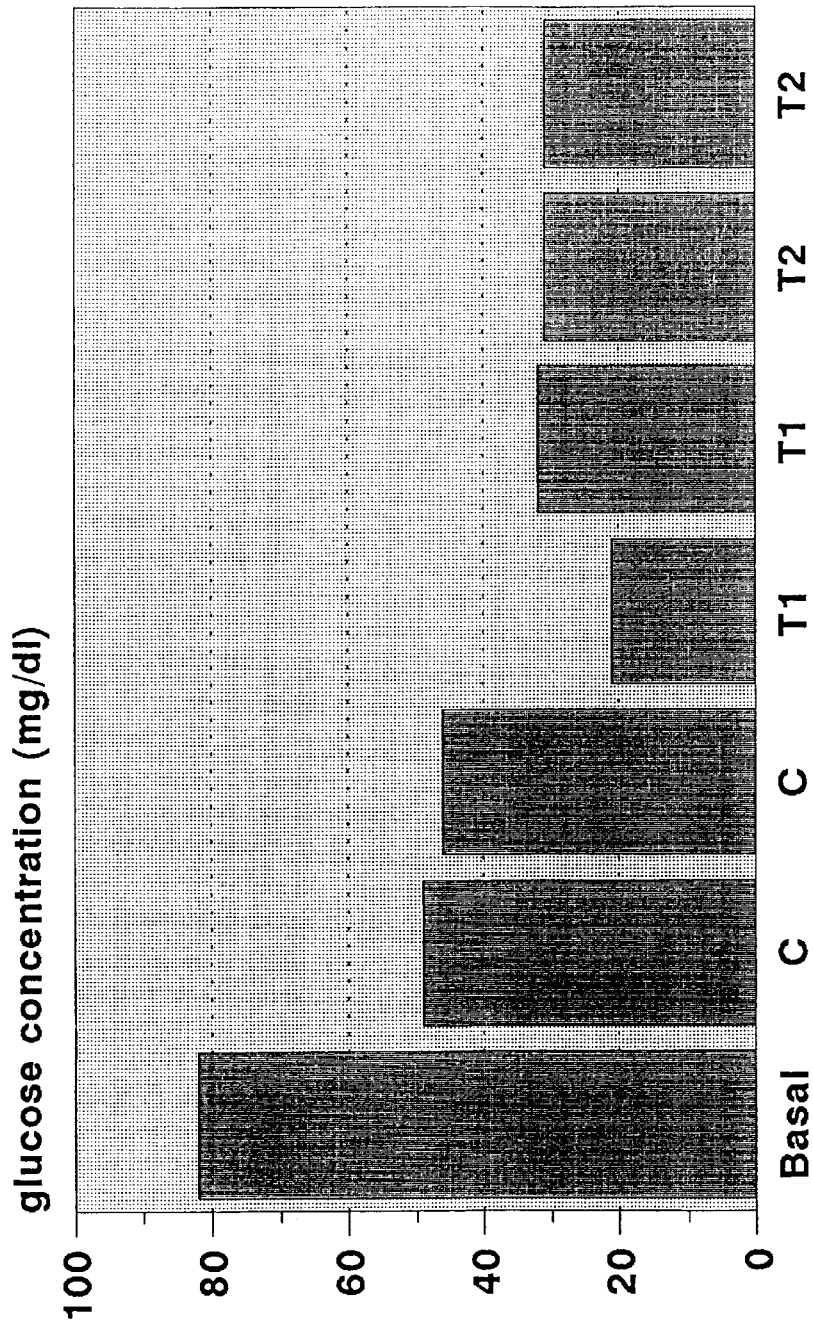
FIG. 1 shows glucose concentrations in culture medium.

Having generally described the invention, reference is now made to the following examples which are intended to illustrated preferred embodiments and comparisons but which are not to be construed as limiting to the scope of this invention as is more broadly set forth above and in the appended claims.

EXAMPLE 1

Glass fabric disks, diameter 2.5 cm and thickness 1.5 mm, composed of fibers 10 μm in diameter and textured by 100×100 μm meshes, are hydrolyzed for 30 minutes in a sterilization apparatus operating at 130° C. Disks are coated by a 0.1–0.2 μm layer of $SiO_2$, modified by Si—$CH_3$ bonds, upon dipping into a 1 M ethanol solution of $CH_3Si(OC_2H_5)_3$ in the presence of aqueous $10^{-3}$ M HCl providing a Si—OR/$H_2O$=1 molar ratio. The solution viscosity ranges in the interval 0.1–5 Pas, the extraction rate is 102 cm/minute. After consolidation for 24 hours at 40° C., the disks are sterilized by steam and placed into 7 cm$^3$ polistyrene wells, 2.5 cm in diameter. Human fibroblasts are obtained by skin biopsy and cultured in Dulbecco's Modified Eagle's Medium (DMEM), supplemented with 10% fetal calf serum (FCS). Two ml of DMEM+10% FCS, containing a suspension of fibroblasts (1×10$^6$ cells/ml) are added to the wells. Cell cultures are incubated at 37° C. for 24 hours. Disks are then transferred in a glass rack and placed into a 5 dm$^3$ reaction chamber equipped for fluxing-gas treatments and suitable for sample collection. Disks re treated with air saturated by bubbling into $Si(OC_2H_5)_4$ and $CH_3SiH(OC_2H_5)_2$ at 80° C., relevant concentration corresponding to 1/1 molar ratio. The total reactive gas flux is 100 cm$^3$/minute and the treatment lasts for 10 or 20 minutes; then, the same flux of air, satured by bubbling into sterile water at 80° C., is passed into the chamber for 10 minutes. The temperature inside the reactor is between 26 and 28° C. The items are transferred into new culture wells containing 2 ml of DMEM+10% FCS and are incubated at 37° C.

The metabolic activity of cultured cells is tested by determination of glucose utilization and of $^3$H-leucine incorporation into secreted proteins. While the former test is an index of energy metabolism, the latter is dependent on the cell ability to take up $^3$H-leucine, incorporate it into proteins and secrete such proteins into the culture medium. Analysis are performed on culture media incubated with the following samples: (1) cells on glass support not subjected to immobilization reaction (used as controls); (2) cells on glass support subjected to 10-min reaction; (3) cells on glass support subjected to 20-min reaction.

Procedure for Metabolic and Morphological Studies

Twenty-four hours after reaction, the culture medium is replaced and incubated with the cells for additional 24 hours. The medium is then aspirated and analysed for glucose concentration by an enzymatic assay. Two ml of medium (DMEM+10% FCS), containing $^3$H-leucine (1 mCi/ml; specific activity of $^3$H-leucine 40.4 GBq/mg) are placed into each well and incubated for 24 hours. At the end of incubation, 1 ml of medium is aspirated from each well and diluted to a final volume of 4 ml with water. The solution is centrifuged at 3000 rpm for 5 min and the supernatant is filtered through 0.45 mm (pore size) filters (Millipore HV), in order to eliminate any particulate matter. The tubes are placed on melting ice and proteins are precipitated from the solution by addition of an equal amount of ice-cold 20% trichloroacetic acid (TCA) solution. After centrifugation, the supernatant is discarded and the pellet is washed three times with 5 ml of ice-cold 10% TCA, in order to eliminate residual $^3$H-leucine. The pellet is finally dissolved in 1 ml 0.5 M NaOH containing 1% sodium duodecylsulphate. One ml of the protein solution is transferred into scintillation vials and added 10 ml of Hionic-Fluor scintillation Fluid (Packard). Four samples (1 ml each) of the original $^3$H-leucine/DMEM+10% FCS solution are processed in the same way and used as blanks. Final $^3$H activity in secreted proteins is calculated by subtracting from each sample the mean of the activities determined in the four blank samples.

Fibroblasts are maintained in culture, changing medium every second day. After one week, supports containing the cells are prepared for scanning electron microscopy (SEM).

Results of Metabolic Studies

Figure 2:
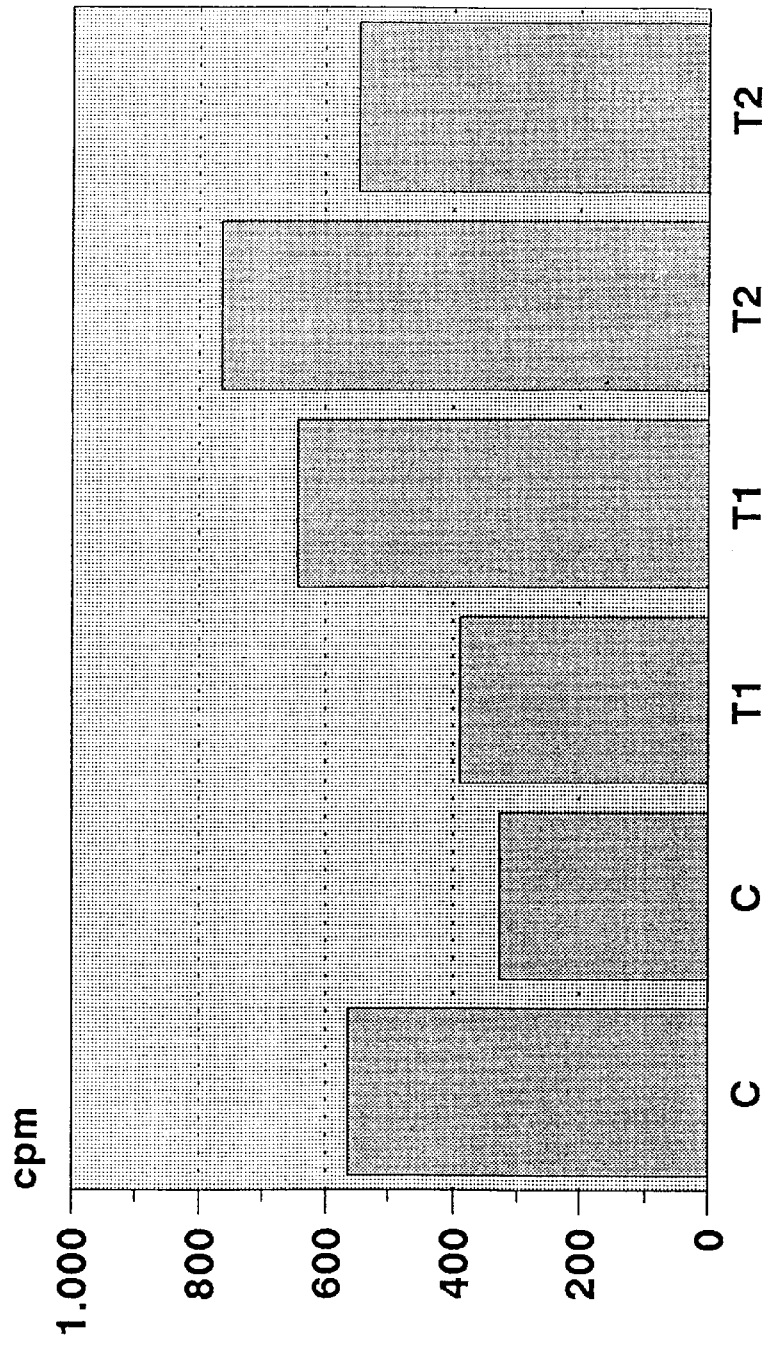
FIG. 2 shows $^3$H activity in proteins secreted into culture medium.

Glucose utilization and $^3$H-leucine incorporation into proteins by cultured human fibroblasts under different experimental conditions are reported in FIGS. 1 and 2 respectively. FIG. 1 shows glucose concentrations in culture medium after 24 hours of incubation with control (non-encapsulated) fibroblasts (C), and with fibroblasts subjected to 10-min (T1) or 20-min (T2) encapsulation reaction. FIG. 2 shows $^3$H activity in proteins secreted into culture medium by the same experimental groups. These results indicate that both glucose utilization and protein synthesis and secretion are well maintained in immobilized encapsulated eufibroblasts.

Results of Morphological Studies

Figure 3:
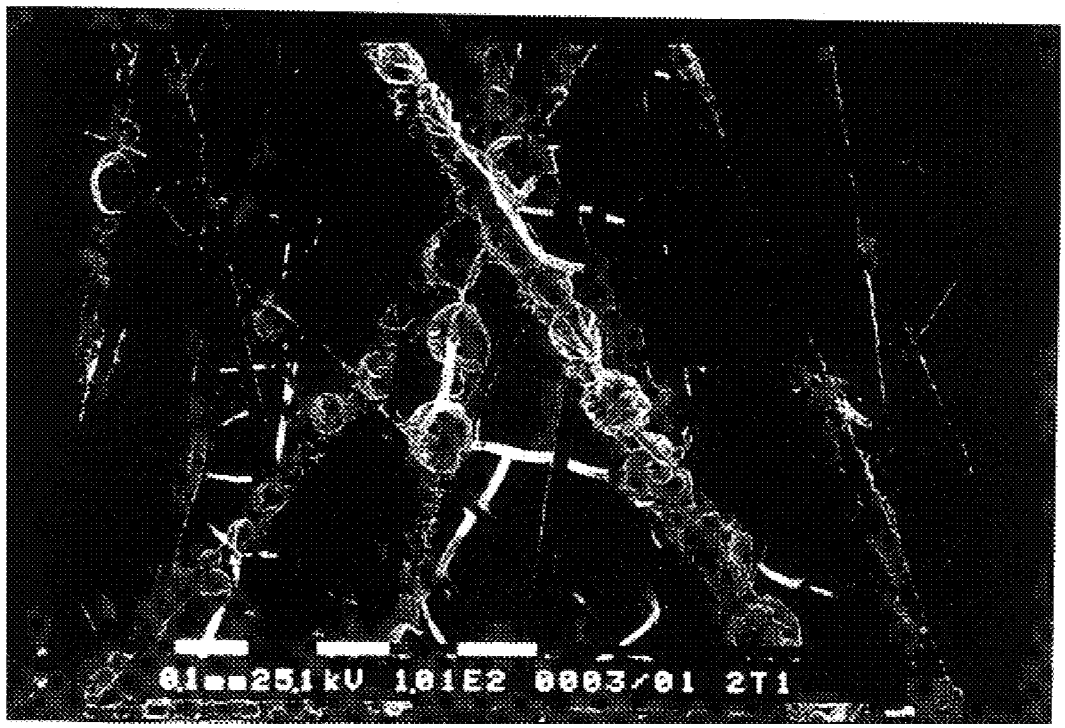
FIG. 3 is a SEM micrograph of clusters of fibroblosts.
Figure 4:
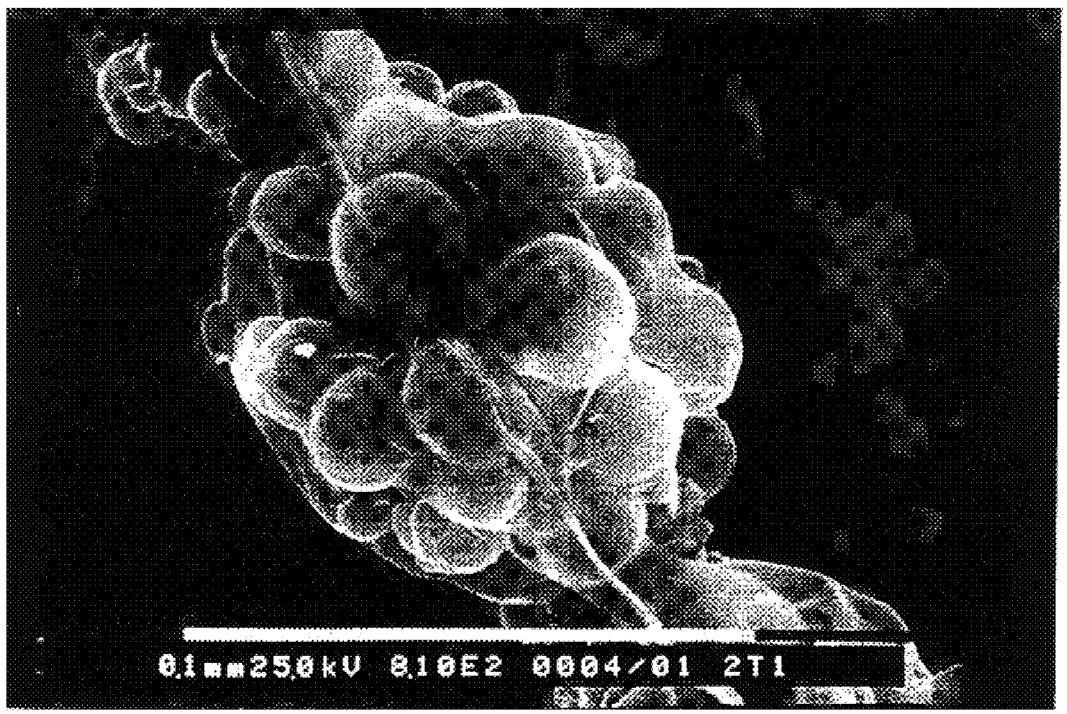
FIG. 4 is a SEM micrograph of encapsulated cell aggregate.

Clusters of fibroblasts enveloped by a silicon oxide membrane are shown in SEM micrographs (FIG. 3). FIG. 4 shows an encapsulated cell aggregate after 10 min of treatment. A transparent silicon oxide layer surrounding a cluster of fibroblasts is clearly evidenced in the micrograph.

EXAMPLE 2

Polyesther rods, diameter 2.5 cm and thickness 0.5 cm, obtained from a continuous sponge-like blanked, are washed until complete release of powdered particles. After drying, rods are placed into polistyrene wells 3 cm in diameter containing 0.6 cm$^3$ of solution composed a 2 M ethanol solution of $CH_3Si(OC_2H_5)_3$ in the presence of $10^{-3}$ M HCl aqueous solution, providing a Si—OR/$H_2O$=2 molar ratio. The systems are left in air at room temperature till gelling of the solution into the bottom surface of rods; these are removed and consolidated at 40° C. for 24 hours. Samples are sterilized by steam at 130° C. for 40 minutes and put into wells, 2.5 cm in diameter and 2.5 cm in depth. Four ml of DMEM+10% FCS, containing a suspension of $25 \times 10^4$/ml H4-II-E-C3 rat hepatoma cells (American Type Culture Collection n° CRL 1600, Rockville, Md.) are then added to the wells. Cells are incubated for 24 hours at 37° C. under 5% $CO_2$, in order to allow cell adhesion and reproduction on rod surface. The rods are then transferred into the gas flux reaction chamber, mentioned in example 1, and here reacted as described in the previous example (reaction time: 20 min). At the end of the reaction, the rods containing the cells are transferred into new wells.

Procedure for Metabolic and Morphological Studies

Test for incorporation of $^3$H-leucine into secreted proteins is performed 48 hours after the reaction as described in example 1. The rods containing the cells are cultured for 7 additional days and then processed for SEM.

Figure 5:
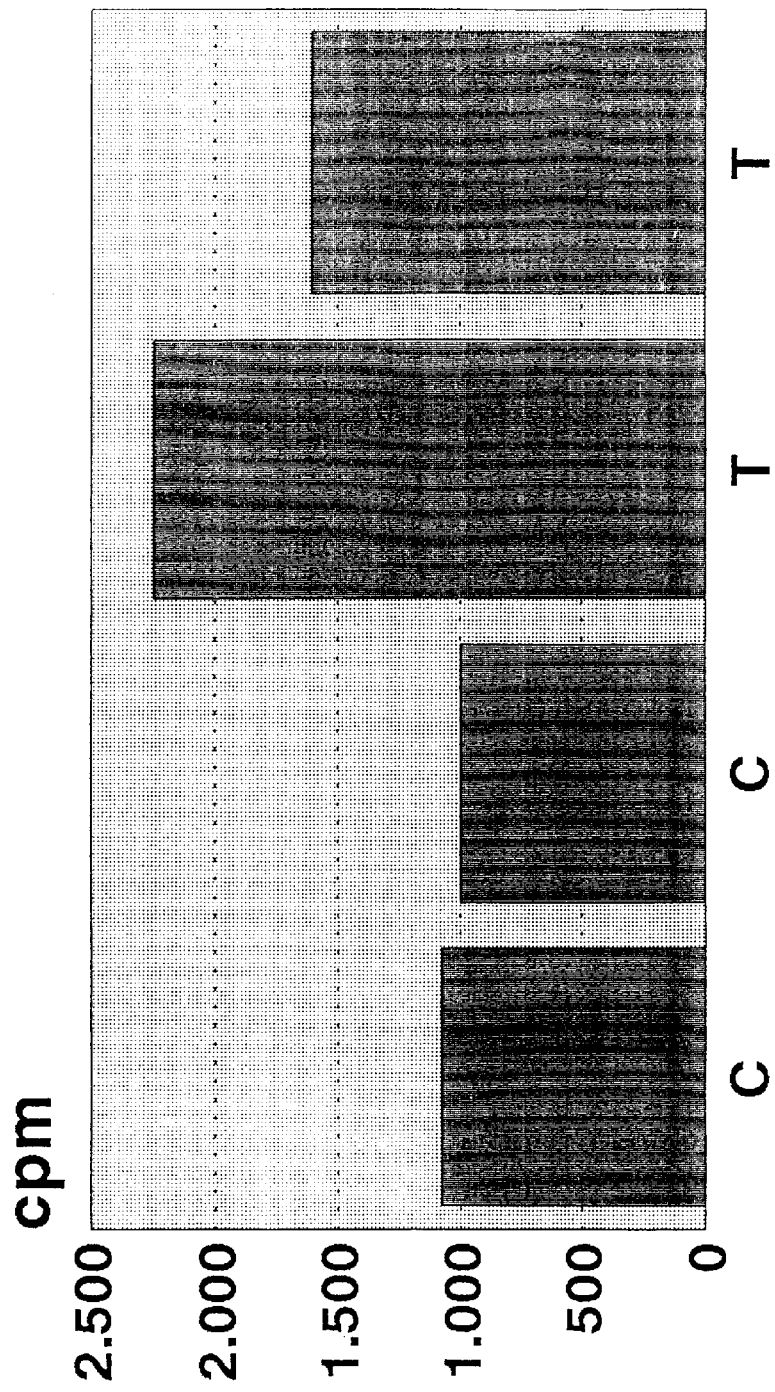
FIG. 5 shows $^3$H activity in proteins secreted by H4 cells.
Figure 6:
FIG. 6 is a SEM micrograph showing a group of H4 cells.

Results of Metabolic and Morphological Studies $^3$H activity in proteins secretd by H4 cells is reported in FIG. 5. The following experimental groups are represented: control (non-encapsulated) cells (C) and encapsulated cells (T). FIG. 6 is a SEM migrograph showing a group of H4 cells growing on polyester fibers. Microprobe analysis reveals a high silicium concentration both on the surface of the cells and on polyester fibers.

EXAMPLE 3

Sterile inorganic membranes, sealed to the bottom of 6 cm$^3$ polistyrene cups, 2.5 cm in diameter, purchased from Nunc Intermed (Roskilde, Denmark) are added 1.5 ml of a suspension of H4 (rat epatoma) cells in DMEM+10% FCS (concentration of $25 \times 10^4$/ml). Cells are allowed to grow on the membrane by incubation for 24 hours at 37° C. under 5% $CO_2$. The liquid medium is poured out and cups are transferred into a 3 dm$^3$ glass reactor and placed in order over a rack, allowing membrane venting on both sides. Some cups are not subjected to reaction and are used as controls. The reactor is equipped with a head, that can be dismantled, and ports for air inlet and outlet and for temperature control. Here, wet samples are invested by an air flux of 100 cm$^3$/minute for 10 minutes, then reacted with a 50 cm$^3$/minute air flux saturated with $Si(OC_2H_5)_4$—$HSiCH_3(OC_2H_5)_2$. Air saturation is performed by bubbling into a $Si(OC_2H_5)_4$/$HSiCH_3(OC_2H_5)_2$=1/1 molar solution, kept at 70° C. by a thermostat. This treatment is prolonged for 10 minutes, then samples are invested by 100 cm$^3$/minute air flux saturated by steam, bubbling into sterile water at 70° C., for 10 minutes. The temperature inside the reactor ranges between 24 and 26° C. Samples are divided into two groups (4 samples per group): (1) no treatment, used as controls; (2) one cycle of treatment. After the reaction, samples are then transferred into new wells in the above-mentioned conditions for 48 hours.

Results of Metabolic and Morphological Studies

Figure 7:
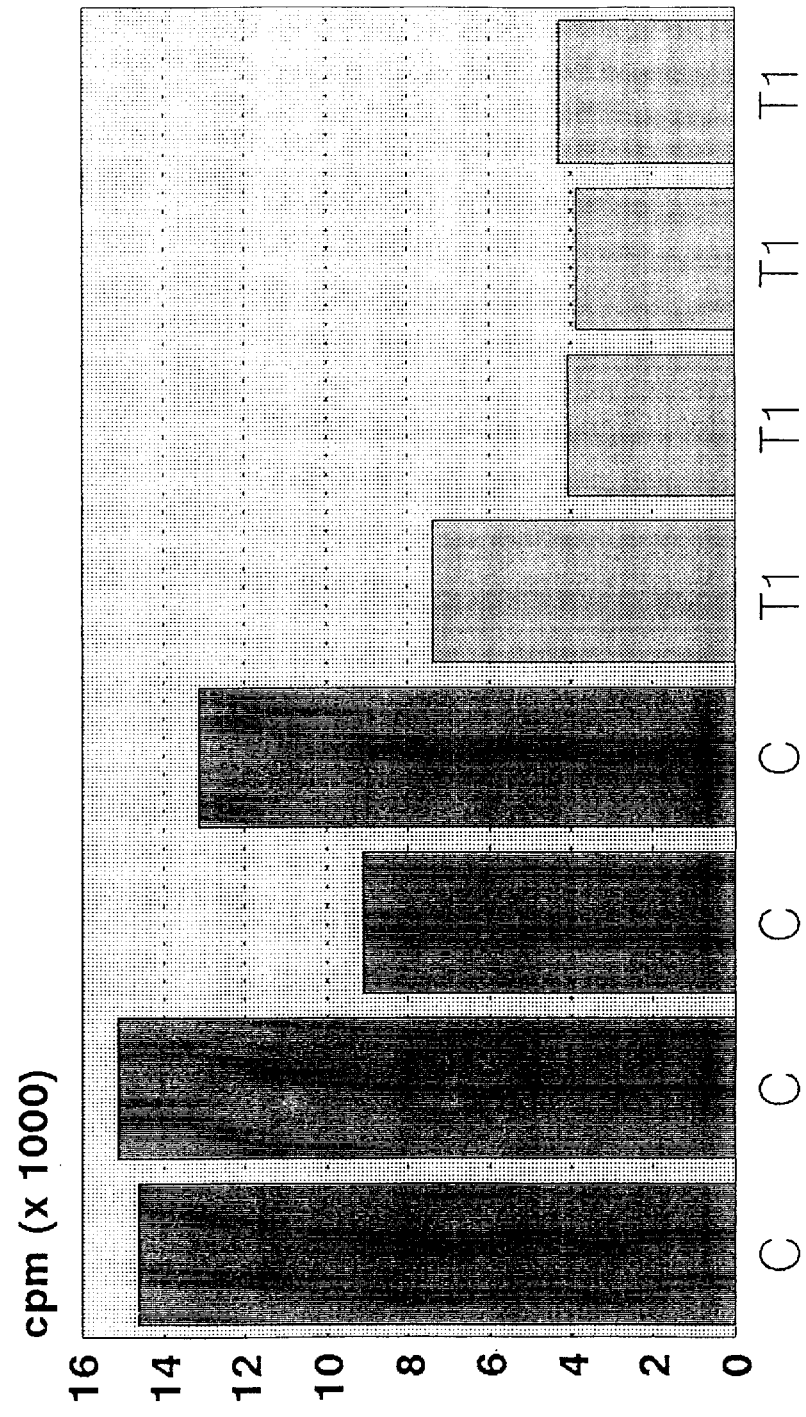
FIG. 7 is a diagram showing incorporation of $^3$H leucine into secreted proteins.
Figure 8:
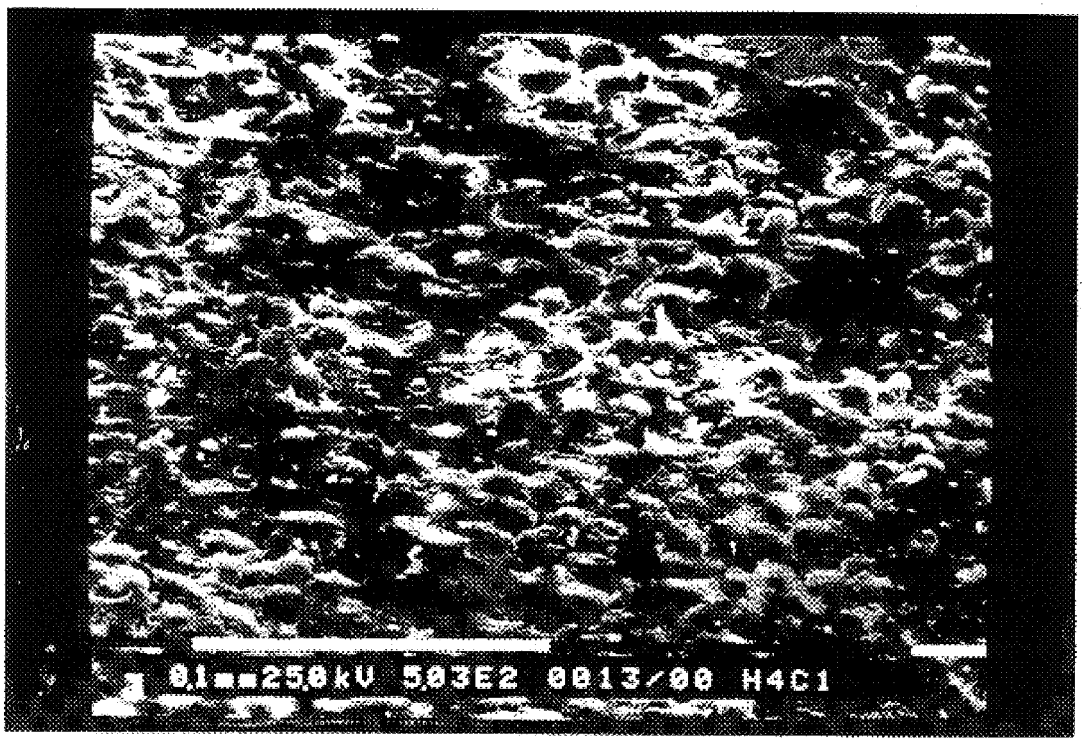
FIG. 8 is a SEM micrograph of control cells.
Figure 9:
FIG. 9 is a SEM micrograph of encapsulated cells.
Figure 10A:
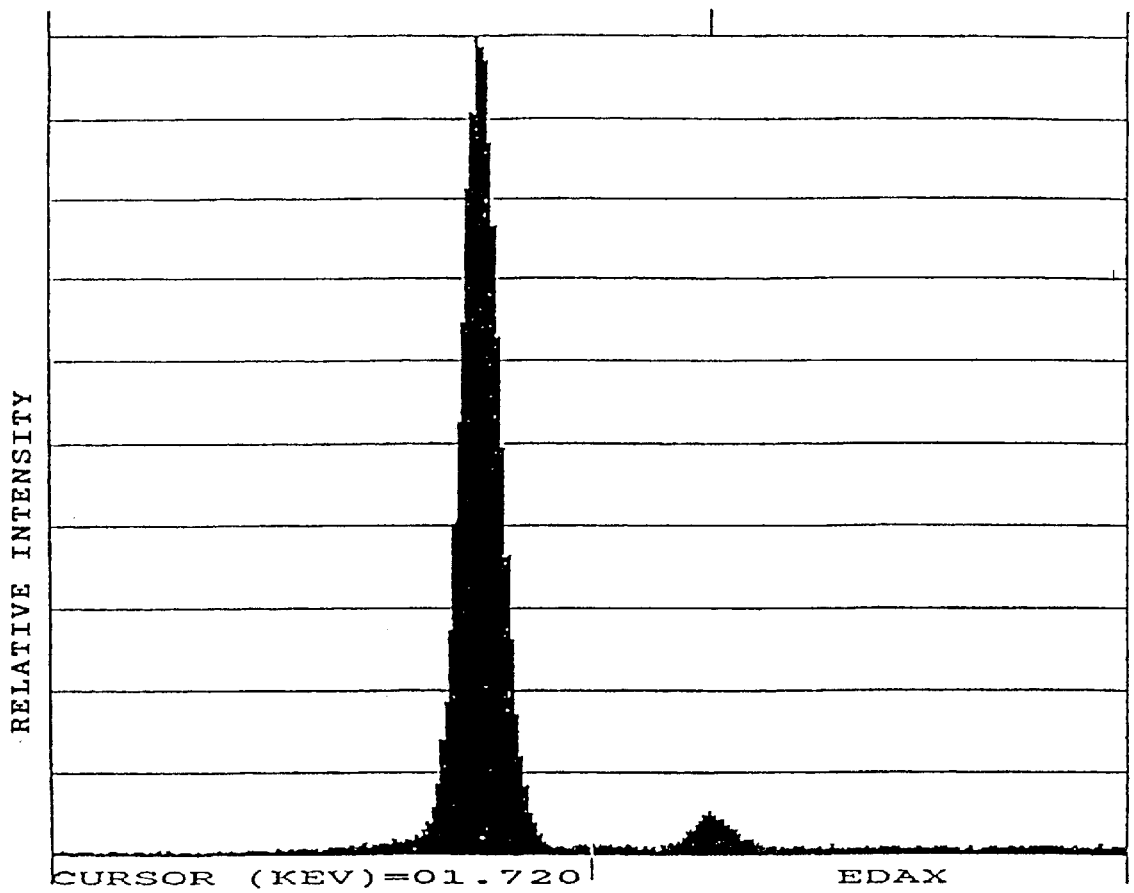
FIG. 10A is a diagram showing a microprobe analysis of support membrane without cells.
Figure 10B:
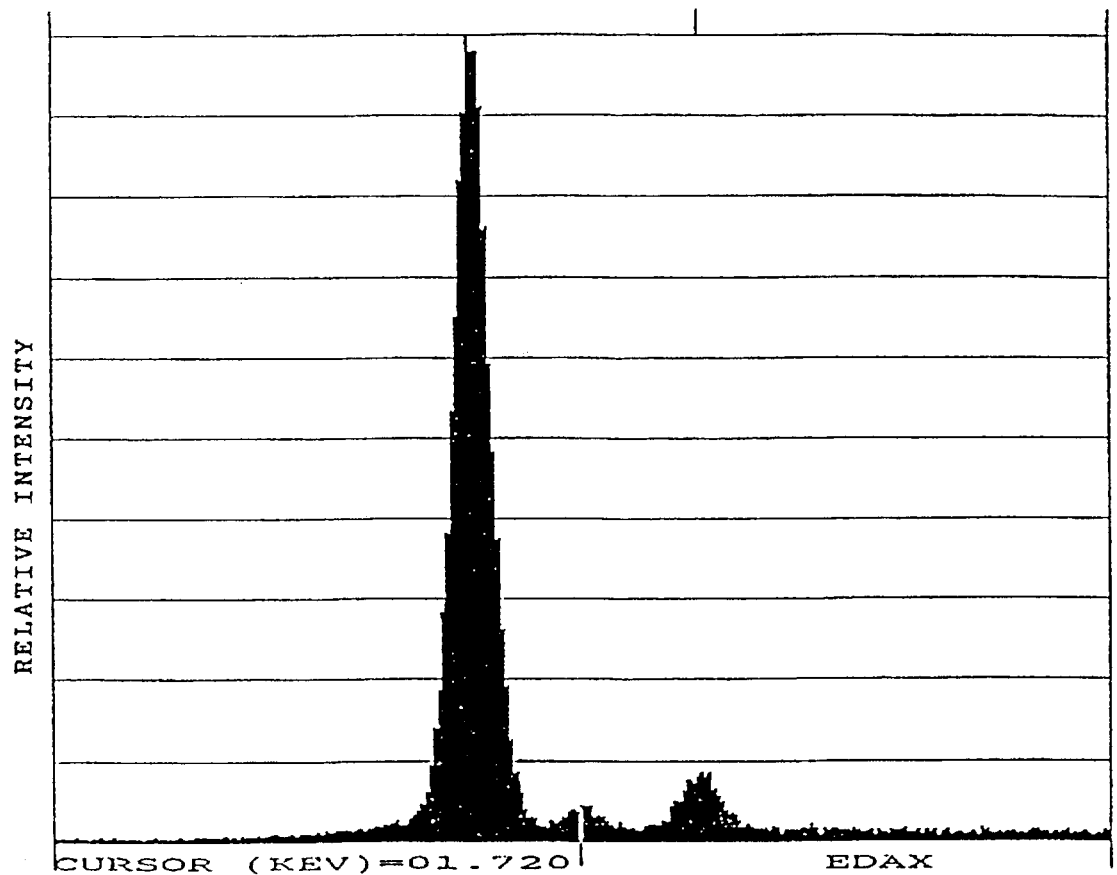
FIG. 10B is a diagram showing a microprobe analysis of a small cell duster on the membrane.

Incorporation of $^3$H-leucine into proteins synthesized and secreted by the cells is then studied as described in example 1. FIG. 7 reports $^3$H activity in proteins secreted by control cells (C) and by encapsulated cells (T). Cells were observed daily by light microscopy. While control cells grew until complete confluence, leaving no free space on the support membrane, encapsulated cells did not grow further, leaving large areas of nude membrane. Such a behaviour is documented by further SEM analysis. FIG. 8 is a SEM micrograph of control cells, forming a continuous layer on the membrane. FIG. 9 is a SEM micrograph of encapsulated cells, showing large non-colonized areas. Microprobe analysis showed silicium deposition on cell surface (FIG. 10A) but not on the inorganic membrane (FIG. 10B), where high concentrations of aluminium and phosphorous were found.

EXAMPLE 4

The same support membranes, mentioned in example 4, are treated with a suspension of HepG2 cells. Cell concentration, culture, reaction conditions, metabolic and morphological studies are identical to those described in example 3.

Figure 11:
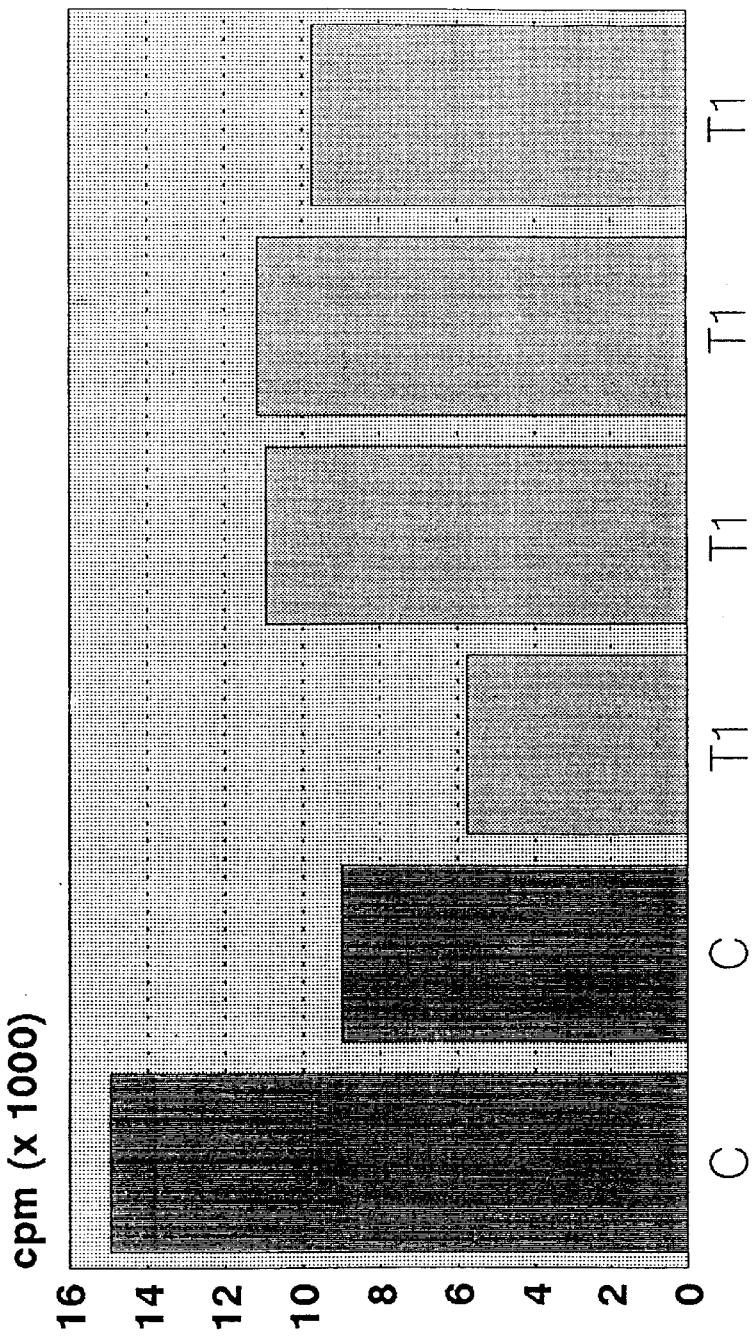
FIG. 11 shows $^3$H leucine incorporation into proteins.

FIG. 11 shows the results of $^3$H-leucine incorporation into proteins secreted by control Hep G2 cells. Morphological aspect of encapsulated cells at SEM was similar to example 3.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A process for encapsulation of viable animal cells suitable for research and industrial applications comprising the steps of:
    a) providing sterilized supports made of organic and/or inorganic compounds and with suitable geometry to immobilize desired loads of cells;
    b) incubating a suspension of viable animal cells with the supports in order to ensure adhesion of the cells to the support surface;
    c) encapsulating the cells with a permanent layer formed by exposing the supports to a reactive gas current composed of a carrier gas saturated by inorganic alkoxides for time intervals suitable to encapsulate said cells and maintain the metabolic activity of said cells after encapsulation;
    d) treating the encapsulated cells with steam under mild hydrolysis conditions while maintain the encapsulation at substantially room temperature to hydrolyze residual alkoxide groups of said inorganic alkoxides; and
    e) storing the cells encapsulated on the supports by immersion into culture media.

2. A process as claimed in claim 1 wherein the reactive gas is composed of a gas carrier saturated by $Si(OR)_4$ and/or $SiX_x(OR)_{4-x}$, where x=1,2; X=H, alkyl or halide; R=alkyl.

3. A process as claimed in claim 1 wherein said supports contain pores and during incubation in step b) growing actively replicating cells fill most of the available volume of the pores.

4. A process as claimed in claim 1 or wherein said layer is continuous and porous, and allows exchange of substances between the cells and the media.

5. A process as claimed in claim 1 wherein said layer contains pores and the pores are sized to exclude direct contact between encapsulated cells and antibodies or immune cells.

6. A process as claimed in claim 1 wherein said supports contain pores and said suspension of cells fills up to the available void volume of the pores.

7. A process as claimed in claim 1 wherein said supports are mounted in extracorporeal devices.

8. A process as claimed in claim 1, wherein said supports are dissolved to yield unsupported encapsulated cells after encapsulation and steam treatment.

9. A process as claimed in claim 1 wherein growth of said cells before encapsulation is stimulated by the addition of hormones or growth factors.

10. A process as claimed in claim 1, wherein said encapsulation step c) is carried out by nebulizing said suspension of cells with said reactive carrier gas.

11. A process as claimed in claim 1, wherein said supports contains pores and are made of materials having a pore size distribution suitable to provide free exchange of nutrients and metabolic products and to avoid antibody and immune-cell interaction when directly implanted into animals or humans.

12. A process as claimed in any one of claims 1, 2–5, 6–8, 9, 10, or 11, wherein the cells are in the form of cell aggregates.

* * * * *